(12) United States Patent  (10) Patent No.: US 7,927,014 B2
Dehler  (45) Date of Patent: Apr. 19, 2011

(54) X-RAY DIAGNOSTIC IMAGING SYSTEM WITH A PLURALITY OF CODED MARKERS

(75) Inventor: Juergen Dehler, Forchheim (DE)

(73) Assignee: Ziehm Imaging GmbH, Nuremberg (DE)

( * ) Notice: Subject to any disclaimer, the term of this patent is extended or adjusted under 35 U.S.C. 154(b) by 0 days.

(21) Appl. No.: 12/114,668

(22) Filed: May 2, 2008

(65) Prior Publication Data

US 2008/0285724 A1  Nov. 20, 2008

(30) Foreign Application Priority Data

May 5, 2007  (DE) .......................... 10 2007 021 185

(51) Int. Cl.
G01D 18/00  (2006.01)
(52) U.S. Cl. ........................................... 378/207; 378/2
(58) Field of Classification Search .......... 378/205–207, 378/2; 235/439, 449
See application file for complete search history.

(56) References Cited

U.S. PATENT DOCUMENTS

| | | | |
|---|---|---|---|
| 4,649,504 A | 3/1987 | Krouglicof et al. | |
| 2001/0053204 A1 | 12/2001 | Navab et al. | |
| 2003/0219102 A1 | 11/2003 | Mitschke et al. | |
| 2005/0281385 A1 | 12/2005 | Johnson et al. | |
| 2006/0109957 A1* | 5/2006 | Lutjens et al. ................ | 378/205 |
| 2006/0115054 A1 | 6/2006 | Yatsenko et al. | |
| 2008/0230608 A1* | 9/2008 | Lallemang .................... | 235/439 |

FOREIGN PATENT DOCUMENTS

| | | |
|---|---|---|
| DE | 197 03 556 | 8/1998 |
| DE | 100 47 382 | 5/2002 |
| DE | 101 39 329 | 3/2003 |
| DE | 102 06 193 | 7/2003 |
| DE | 102 02 091 | 8/2003 |
| DE | 102 15 808 | 11/2003 |
| DE | 103 52 556 | 6/2005 |
| DE | 103 60 025 | 7/2005 |
| DE | 10 2007 021183 | 11/2008 |
| DE | 10 2007 021185 | 11/2008 |
| EP | 1 990 004 | 11/2008 |
| EP | 1 990 008 | 11/2008 |
| JP | 2002 024781 | 1/2002 |
| WO | WO 2004/052205 | 6/2004 |
| WO | WO 2006/130012 | 12/2006 |

OTHER PUBLICATIONS

European Search Report, EP 1 990 008, Sep. 5, 2008, 3 pages.

* cited by examiner

*Primary Examiner* — Hoon Song
(74) *Attorney, Agent, or Firm* — Knobbe, Martens, Olson & Bear LLP

(57) ABSTRACT

Embodiments of an X-ray diagnostic imaging system comprise a plurality of coded 2D and/or 3D markers associated with surfaces of system components. The position and coding of at least some of the coded markers can be determined by a position detection system. In some embodiments, a coded marker is assigned a reference point having a known position on the surface of the system component. The positions of the system components in space can be calculated based at least in part on a reference point network determined from the position of the individual reference points measured with the position detection system. In some embodiments, the coded markers represent information with a data matrix code (DMC).

10 Claims, 2 Drawing Sheets

US 7,927,014 B2

X-RAY DIAGNOSTIC IMAGING SYSTEM WITH A PLURALITY OF CODED MARKERS

CROSS-REFERENCE TO RELATED APPLICATIONS

This application claims the right of priority under 35 U.S.C. §119(a)-(d) to German Patent Application No. DE 10 2007 021 185.8, filed May 5, 2007, the entire disclosure of which is hereby incorporated by reference herein and made part of this specification.

BACKGROUND

1. Field

The disclosure relates generally to an X-ray diagnostic imaging system with a marker arrangement on surfaces of system components and methods for determining positions of the system components.

2. Description of the Related Art

Medical interventions involving living subjects are increasingly performed using navigation assistance provided by a navigation system. In some navigation systems, a surgical instrument is guided by means of a position detection system relative to a tissue region of the subject undergoing treatment. Navigation assistance is of particular interest in body regions that cannot be visually inspected by the surgeon, such as when the instrument is inserted into the interior of the subject. For this purpose, the instrument, for example, a catheter, is guided in a virtual 3D volume generated by means of an imaging method prior to or during surgery. For example, an X-ray diagnostic machine may be used to generate a series of 2D projection images having a known projection geometry, and the 2D images may be used to generate a 3D volume data set. The 3D volume data set is transmitted to the navigation system, which is equipped with a position detection system for detecting positions of the markers. For high-precision navigation, the coordinate system of the position detection system can be aligned and/or oriented with the coordinate system of the 3D volume data set in a process commonly known as "registration."

Various X-ray diagnostic devices are known in which a portion of the device is provided with marks that can be detected by a position detection system.

German Patent DE 102 06 193 C1 discloses an X-ray diagnostic imaging system in which a marker arrangement in the form of a two-dimensional barcode is used. No correlation of the coded information to the position of the barcode on the housing is provided in a fixed coordinate system of the device.

German Patent DE 102 15 808 B4 describes an X-ray device having a mark arrangement on the holder for a C-arm. The mark arrangement can be detected with a position detection system, and the spatial configuration and position of the X-ray device can be determined.

German Patents DE 103 60 025 B4 and DE 101 39 329 B4 describe X-ray diagnosis devices in which an X-ray receiver has a mark arrangement.

German Patent DE 103 52 556 A1 (Offenlegungsschrift) discloses a coded marker arrangement for identifying and positioning patients.

U.S. Pat. No. 4,649,504 discloses an optical method for determining the position and orientation of a solid body with markers.

PCT Patent Publication WO 2006/130012 discloses a method for the pre-transformation and linearization of a pixel matrix for use with an automatic optical character recognition (OCR) system.

For some X-ray diagnostic imaging systems with marker arrangements on the surface of system components, generally only a few markers are provided within the angular detection range of the position detection system. Additionally, only a small number of markers can be evaluated if the position detection system is unfavorably positioned relative to the X-ray diagnostic imaging system. The accuracy of the position measurement may be limited in such systems.

SUMMARY

Because of the foregoing (and other) challenges and limitations, there is a need to improve accuracy of the measurement of positions of system components of an X-ray diagnostic imaging system. In certain embodiments of the disclosed systems and methods, a large number of coded markers that can be detected and distinguished are distributed over the surface of the X-ray diagnostic imaging system (or system component). Each coded marker has a reference point on the surface and a code associated therewith such that the reference point can be correlated with a predetermined location on the surface of the X-ray diagnostic imaging system (or system component). The measured positions of the reference points can be used to determine, for example, the position and/or orientation of system components, X-ray projection geometries, and so forth.

In some embodiments, an X-ray diagnostic imaging system comprises a plurality of coded 2D and/or 3D markers associated with surfaces of system components. The position and coding of at least some of the coded markers can be determined by a position detection system. In some embodiments, a coded marker is assigned a reference point having a known position on the surface of the system component. The positions of the system components in space can be calculated based at least in part on a reference point network determined from the position of the individual reference points measured with the position detection system. In some embodiments, the coded markers represent information with a data matrix code (DMC).

In an embodiment of an X-ray diagnostic imaging system with a control computer and one or more system components, the X-ray diagnostic imaging system comprises a plurality of markers detectable by a position detection system. Each marker is associated with a surface of a housing of a system component. The embodiment of the X-ray diagnostic imaging system is characterized in that each marker comprises a 2D code that represents a reference point on the surface of the housing, and the code for each reference point is associated with a position of the respective reference point on the surface. The code may be stored in a look-up table accessible by the control computer.

In certain embodiments, the X-ray diagnostic imaging system is characterized in that the 2D code of the markers is arranged on a planar surface or developed on a curved surface.

In certain embodiments, the X-ray diagnostic imaging system is characterized in that at least some of the plurality of markers comprise auto-reflection markers that are printed or bonded on the surface.

In certain embodiments, the X-ray diagnostic imaging system is characterized in that at least some of the plurality of markers are integrated into their respective housings as LED markers or optical fiber markers such that the markers appear on the surfaces of the housings as punctiform light sources.

In certain embodiments, the X-ray diagnostic imaging system is characterized in that the 2D code comprises a data matrix code.

In certain embodiments, the X-ray diagnostic imaging system is characterized in that the 2D codes are nested into one another and have different outside dimensions.

An embodiment of a method for determining positions of one or more system components of an X-ray diagnostic imaging system having a position detection system and a control computer is provided. The positions may be determined with respect to coordinate systems of the position detection system and the X-ray diagnostic imaging system. In some embodiments, the method comprises recording with a camera of the position detection system at least one image of markers associated with the X-ray diagnostic imaging system. Each marker comprises a 2D code that represents a reference point on a surface of a housing of a system component. The method further comprises carrying out a pre-transformation for each marker in the image to obtain a respective orthogonal marker image. The location of the reference point in the original image may be preserved in the orthogonal marker image. The method further comprises automatically recognizing the codes in the orthogonal marker images and correlating the code to the positions of the reference points in the coordinate system of the position detection system. The method further comprises communicating the positions of the reference points and the correlated code to the control computer, and calculating positions of the system components in a coordinate system of the X-ray diagnostic imaging system. The calculated positions in the coordinate system of the X-ray diagnostic system are based at least in part on a look-up table storing the positions of the reference points on the surfaces of the system components.

BRIEF DESCRIPTION OF THE DRAWINGS

The following drawings and the associated descriptions are provided to illustrate embodiments of the present disclosure and do not limit the scope of the claims.

DETAILED DESCRIPTION OF PREFERRED EMBODIMENTS

Figure 1:
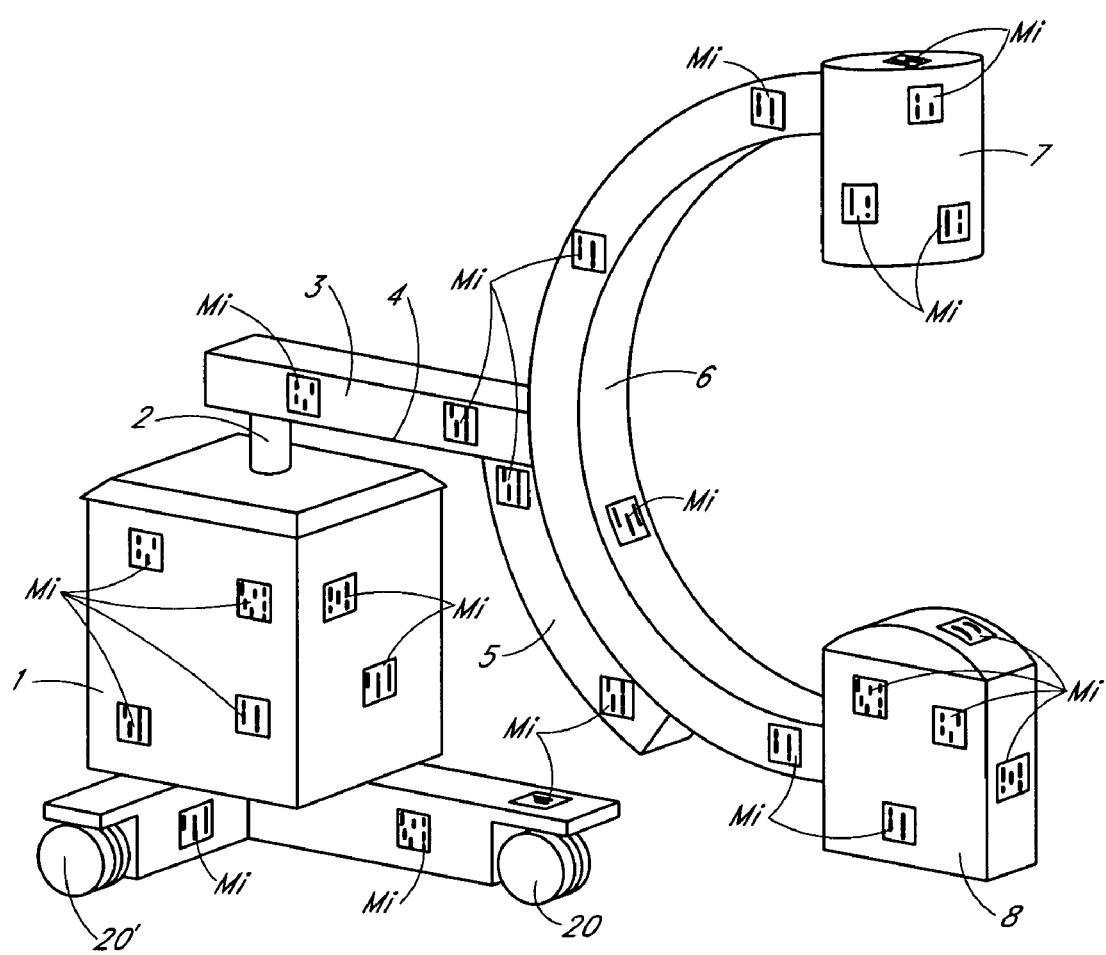
FIG. 1 schematically illustrates an embodiment of a mobile X-ray diagnostic imaging system having a plurality of coded markers distributed on surfaces of system components.

FIG. 1 schematically illustrates an embodiment of a mobile X-ray diagnostic imaging system comprising a cart 1 that can be moved along the floor on rollers 20, 20'. The imaging system comprises a C-arm 6 that is mounted to the cart 1 with C-arm mount 5. The C-arm 6 can be adjusted in multiple ways. The C-arm 6 is movable along its circumference about a center of the C-arm 6. The C-arm mount 5 is supported on a horizontally displaceable horizontal guide 3 with a pivot bearing 4, which permits the C-arm 6 to be pivoted about a horizontal axis. The horizontal guide 3 is supported on a column 2, which can be adjusted in height and rotated about the vertical axis of the column 2. An X-ray source 8 and an X-ray receiver 7 are disposed on opposing ends of the C-arm 6.

In the embodiment illustrated in FIG. 1, a plurality of coded markers Mi is distributed over surfaces of various components of the X-ray diagnostic imaging system. For example, as shown in FIG. 1, the markers Mi may be attached to surfaces of housings of the system components 1, 3, 5, 6, 7, and 8. The markers Mi may be attached to other surfaces of the X-ray diagnostic imaging system (or system components). FIG. 1 schematically illustrates one possible arrangement of markers Mi on the X-ray diagnostic imaging system. Other marker arrangements are possible. In other embodiments, a larger or smaller number of markers Mi may be used compared to the example shown in FIG. 1. Some or all of the markers Mi can be detected by a position detection system (not shown in FIG. 1).

Figure 2A:
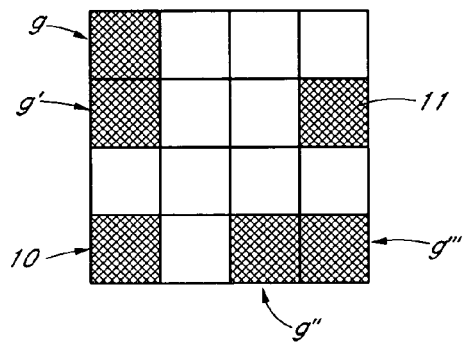
FIGS. 2a-2c schematically illustrate examples of coded markers comprising a two-dimensional (2D) matrix code.
Figure 2B:
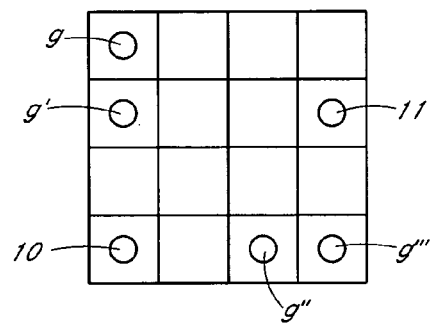
Figure 2C:
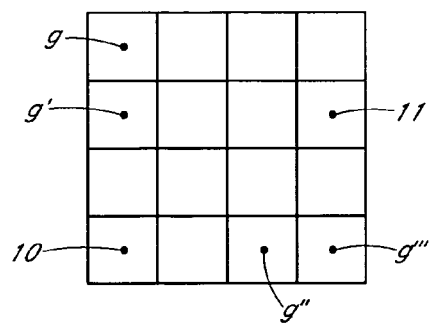

FIGS. 2a-2c schematically illustrate examples of coded markers Mi comprising a two-dimensional (2D) matrix code. In the illustrated examples, a 2D marker Mi comprises a reference marker 10, position markers 9, 9', 9", and 9''', and a coding marker 11 in a coding range that comprises 9 fields. FIGS. 2a-2c illustrate one example arrangement of the markers 9-9''', 10, and 11 to represent a particular code. The markers 9-9''', 10, and 11 may be arranged differently to represent different codes than illustrated in FIGS. 2a-2c. In these embodiments, the markers 9-9''', 10, and 11 are arranged in a 2D grid. The markers may have any suitable shape such as, for example, squares (FIG. 2a), circles (FIG. 2b), and/or points (e.g., punctiform, FIG. 2c). In some embodiments, some or all of the markers 9-9''', 10, and 11 may be shaped differently from each other. In some embodiments, the position markers 9-9''' may be shaped differently from the reference marker 10, which is shaped differently from the coding marker 11. In other embodiments, other shapes or combinations of shapes may be used.

Figure 4A:
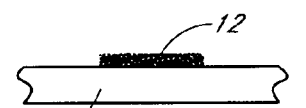
FIGS. 4a-4d schematically illustrate different examples of how markers may be associated with a surface of a housing.
Figure 4B:
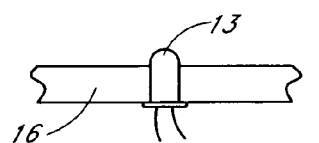
Figure 4C:
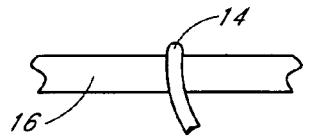
Figure 4D:
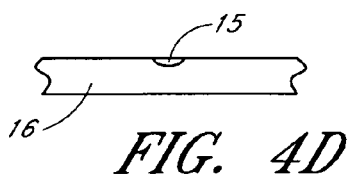

FIGS. 4a-4d schematically illustrate different possible examples of how the markers 9-9''', 10, and 11 may be associated with a surface of a housing of a system component. For example, FIG. 4a shows a marker applied to the surface of a housing 16 as an auto-reflection marker 12. The auto-reflection marker 12 may be formed by printing and/or bonding in some embodiments. A marker may comprise a light source, for example, a light-emitting diode (LED) marker 13 (shown in FIG. 4b) or an optical fiber marker 14 (shown in FIG. 4c). The light source (such as the optical fiber) may terminate in a microlens. A marker may comprise a sensing depression 15 (shown in FIG. 4d) that can be scanned with a pointer of a position detection system. Markers may be formed in other methods in other embodiments. Further, some or all of the markers 9-9''', 10, and 11 may be formed differently from each other.

Figure 3:
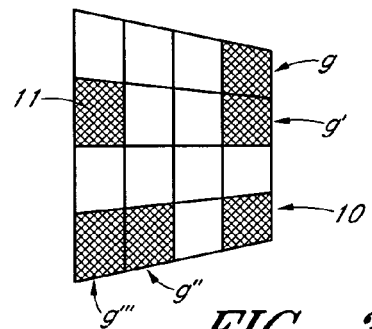
FIG. 3 schematically illustrates the appearance of the example marker shown in FIG. 2a as viewed obliquely relative to the plane of the marker.

In some example methods, a position detection system is used for reading the marker code and for determining the position of the reference marker 10. The position detection system may comprise a camera or a stereo camera and one or more images of the markers Mi may be recorded. The recorded images may be stored on any suitable computer-readable medium. FIG. 3 schematically illustrates the appearance of the example marker shown in FIG. 2a as viewed obliquely relative to the plane of the marker. In certain embodiments, some or all of the markers Mi in a recorded image are initially individually subjected to a pre-transformation in which an image of a marker Mi that is disposed on an inclined and/or curved surface is transformed into an orthogonal marker image that represents the marker as if viewed from a direction orthogonal to the marker plane. In some embodiments, the pre-transformation preserves the location of the reference marker 10 in the complete image. In certain embodiments, after the pre-transformation is performed, the marker code is decoded using a known stored key. Positions of the reference markers 10 in a coordinate system of the X-ray diagnostic imaging system (or in a coordinate system of the system components) are stored for the decrypted codes of the markers Mi. For example, in one embodiment, the positions of the reference markers 10 are stored in a look-up table (LUT). In certain embodiments, the code that can be determined based on the values determined by the position detection system is linked to the position of a defined reference point on the surface of a system component of the X-ray diagnostic imaging system.

In various embodiments, the markers Mi may comprise a planar 2D code or a 3D code in the form of a 2D code developed on a curved surface. In some embodiments, for example, barcodes or data matrix codes (DMC) may be used as codes. The reference point on the surface that is associated with a particular marker Mi may form part of the code according to a code convention and/or may be defined as a geometric shape in the marker Mi (e.g., a circle, a square, a point, a reticle, etc.). In some embodiments, some or all of the markers Mi are arranged substantially seamlessly adjacent to each another on the surface of the X-ray diagnostic imaging system (or system components).

A general and/or special purpose computer may be used, for example, to perform the pre-transformation (if used), to decode the markers Mi, and to determine the LUTs, and to calculate positions of the markers and system components in a suitable coordinate system. For example, evaluation of the measurement of the coded markers obtained with the position detection system permits a reconstruction of a reference point network for the surfaces. In embodiments in which the positions of the reference points on the surfaces are known, the position and/or orientation of the system components in space relative to the coordinate system of the position measuring system may be determined. Additionally, in some embodiments, the position of some or all of the individual system components and their orientation relative to each other may be determined. In various embodiments, such position and/or orientation information may be used for determining X-ray projection geometries.

Although described herein in the context of an X-ray diagnostic imaging system, a person of ordinary skill will recognize that embodiments disclosed herein may be used with other medical devices. Methods and processes described herein may be embodied in, and partially or fully automated via, software code modules executed by one or more general and/or special purpose computers. The word "module" refers to logic embodied in hardware and/or firmware, or to a collection of software instructions written in a programming language. Software code modules may be stored on any suitable type of computer-readable medium. In any method or process disclosed herein, the acts or operations of the method or process may be performed in any suitable sequence and are not necessarily limited to any particular disclosed sequence. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner in one or more embodiments, as would be apparent to one of ordinary skill in the art from this disclosure. Additionally, although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. An X-ray diagnostic imaging system with a control computer and one or more system components, the X-ray diagnostic imaging system comprising a plurality of markers detectable by a position detection system, each marker associated with a surface of a housing of a system component,
   characterized in that the surface comprises at least one curved portion, wherein multiple markers are positioned on the curved portion and arranged substantially seamlessly across the curved portion, wherein each marker comprises a 2D code that represents the position of a reference point on the surface of the housing, wherein each marker is pre-transformed to an orthogonal marker image that represents the marker as if viewed from a direction orthogonal to the marker, wherein the 2D code on the orthogonal marker image can be decrypted, and correlated with stored codes in a look-up table accessible by the control computer, wherein each stored code correlates with a predetermined location on the surface of the X-ray diagnostic imaging system.

2. The X-ray diagnostic imaging system according to claim 1, characterized in that the surface comprises a planar portion.

3. The X-ray diagnostic imaging system according to claim 1, characterized in that at least some of the plurality of markers comprise auto-reflection markers that are printed or bonded on the surface.

4. The X-ray diagnostic imaging system according to claim 1, characterized in that at least some of the plurality of markers are integrated into their respective housings as LED markers or optical fiber markers such that the markers appear on the surfaces of the housings as punctiform light sources.

5. The X-ray diagnostic imaging system according to claim 1, characterized in that the 2D code comprises a data matrix code.

6. The X-ray diagnostic imaging system according to claim 1, characterized in that the 2D codes are nested into one another and have different outside dimensions.

7. A method for determining positions of one or more system components of an X-ray diagnostic imaging system having a position detection system and a control computer, the positions determined with respect to coordinate systems of the position detection system and the X-ray diagnostic imaging system, the method comprising:
   recording with a camera of the position detection system at least one image of a network of markers associated with the X-ray diagnostic imaging system, each marker comprising a 2D code that represents a reference point on a curved surface of a housing of a system component;
   carrying out a pre-transformation for each marker in the image to obtain a respective orthogonal marker image, wherein the location of the reference point in the original image is preserved in the orthogonal marker image;

automatically recognizing the 2D codes in the orthogonal marker images and correlating the 2D codes to the positions of the reference points in the coordinate system of the position detection system;

communicating the positions of the reference points and the correlated 2D code to the control computer; and calculating positions of the system components in a coordinate system of the X-ray diagnostic imaging system based at least in part on a look-up table storing the positions of the reference points on the surfaces of the system components.

8. The method of claim 7, wherein at least some of the markers comprise auto-reflection markers that are printed or bonded on the surface.

9. The method of claim 7, wherein at least some of the markers are integrated into their respective housings as LED markers or optical fiber markers such that the markers appear on the surfaces of the housings as punctiform light sources.

10. The method of claim 7, wherein the 2D code comprises a data matrix code.

* * * * *